United States Patent [19]

McAulay et al.

[11] Patent Number: 5,663,799
[45] Date of Patent: Sep. 2, 1997

[54] OPTICAL DIFFRACTION METHOD AND APPARATUS FOR INTEGRATED CIRCUIT LEAD INSPECTION

[75] Inventors: Alastair D. McAulay, Allentown; Junqing Wang, Bethlehem, both of Pa.

[73] Assignee: Competitive Technologies of PA, Inc., Bethlehem, Pa.

[21] Appl. No.: 590,495

[22] Filed: Jan. 24, 1996

[51] Int. Cl.[6] .......................... G01B 11/00; G01N 21/00
[52] U.S. Cl. .......................... 356/398; 356/237; 250/237.6
[58] Field of Search .......................... 356/398, 237; 250/237.6

[56] References Cited

U.S. PATENT DOCUMENTS

| | | | |
|---|---|---|---|
| 4,696,047 | 9/1987 | Christian et al. | 382/8 |
| 4,875,778 | 10/1989 | Luebbe et al. | 356/394 |
| 4,875,779 | 10/1989 | Luebbe et al. | 356/394 |
| 5,162,866 | 11/1992 | Tomiya et al. | 356/237 |
| 5,212,390 | 5/1993 | LeBeau et al. | 250/561 |
| 5,309,223 | 5/1994 | Konicek et al. | 356/375 |
| 5,331,406 | 7/1994 | Fishbaine et al. | 356/375 |

OTHER PUBLICATIONS

Choudhury, D., Acharya, T.K., and Ghosh, A., "Self-imaging by an Amplitude Grating Followed by a Glass Wedge and its Application in Image Substraction", Optics Communications 98 (1993) pp. 245–249.

Sakuma, H., Furukawa, Y., Okada, T., Tanabe, K., and Ueno, S., "Image Processing for Visual Inspection of Connector-Plug-Pins Using Neural Networks", Journal of the Japan Society of Precision Engineering vol: 59 Iss: 8 (1993) pp. 1865–1870.

Kashitani, A., Takanashi, N., and Tagawa, N., "A Solder Joint Inspection System for Surface Mounted Pin Grid Arrays", IEOCN '93, Int'l Conf. on Industrial Electronics Control and Instrumentation, vol. 3 (1993) pp. 1865–1870.

McAulay, A.D., "Optical Computer Architectures: The Application of Optical Concepts to Next Generation Computers", John Wiley & Sons, Inc. (1991) pp. 472–477.

Patorski, K., "The Self-Imaging Phenomenon and It's Applications" *Progress in Optics vol. XXVII* Edited By E. Wolf, Elsevier Science Publishers B.V., 1989, pp. 3–108.

Siebert, W. "Circuits, Signals and Systems" McGraw-Hill 1986 pp. 369–373.

Primary Examiner—Frank G. Font
Assistant Examiner—Amanda Merlino
Attorney, Agent, or Firm—Michael R. Novack

[57] ABSTRACT

A technique for detecting damage of leads arranged in a generally parallel periodic pattern, includes the following steps: directing a coherent light beam at a plurality of adjacent leads; detecting an image at a distance from the leads at which the light beam would form a diffraction image having substantially uniform intensity when the leads form a substantially uniform pattern; moving the pattern of leads and the light beam with respect to each other; and detecting damage of leads from variation in intensity of the detected image.

20 Claims, 7 Drawing Sheets

LEAD SHIFTED
TO RIGHT
BY 50%

FIG. 6A

MISSING
LEAD

FIG. 7A

LEAD SHIFTED
TO RIGHT
BY 12.5%

OPTICAL DIFFRACTION METHOD AND APPARATUS FOR INTEGRATED CIRCUIT LEAD INSPECTION

FIELD OF THE INVENTION

The present invention relates to an improved method and apparatus for inspecting the lead integrity of integrated circuit chips.

BACKGROUND

Very large scale integrated (VLSI) circuit semiconductor chips are used in a wide variety of applications (e.g., computers, appliances, automobiles, etc.) and are manufactured in extremely large quantities. One or more VLSI chips are often mounted on a circuit board. As indicated by the very name, VLSI chips are highly integrated and incorporate a multiplicity of electronic functions. The continuing trend of VLSI chip manufacturing is toward further integration and miniaturization. As a consequence of their small size, VLSI chips are often created in a configuration referred to as quad flat packs (QFP's) or quad packs with closely spaced leads (the term "lead" and "pin" being used interchangeably) emanating from each side of the quad pack.

The connecting leads on the outer edge of the chips often exceed 80 leads per side and have a lead period (the center to center distance of two adjacent leads) of the order of 200 to 300 microns. As mentioned above, the present trend is towards further miniaturization of the chips, which will require an increased number of leads per chip, and smaller lead periods. The delicate nature of the leads makes them vulnerable to various kinds of damage such as bending, twisting and breaking. Damage to the leads can occur during the production, packing and transportation of the chip and, more often, during the assembly process.

Surface Mount Technology (SMT) is presently the most common assembly process for mounting chips onto a circuit board. The connecting leads of a chip are placed on special contact pads on the top surface of the circuit board. After mounting, the leads are soldered. QFP's are particularly configured for surface mounting with special leads often referred to as gull wings. It is necessary that the QFP's are accurately placed by pick and place machines onto the surface of the circuit board with the gull wing leads making proper contact with the pads. Typically, a large number of chips are assembled onto a single board and then flow soldered. If a single lead on any one chip is damaged, the entire board is rejected. A damaged lead is a lead, that after soldering does not make correct contact with the pad on the circuit board (causing an open circuit or a higher than acceptable impedance), or a lead that touches an adjacent lead causing a short circuit (or come so close as to interfere with correct operation). Given the size of the leads and the distance between them, there is a significant possibility for lead damage to occur during the high speed placement process.

As mentioned above, chips are plucked from a spool by an automated machine and are placed onto a circuit board. Currently the fastest assembly machines move at a rate of approximately 2 meters/second. In order to prevent large scale rejection of finished circuit boards, it is optimal to perform inspection of the leads after the chip has been picked from the spool, and prior to placement on the circuit board.

Conventional vision systems, such as those used in component placement machines have been suggested as one solution. These systems utilize solid state television cameras to capture an image of the leads under examination, and include a means to compare the captured image with a reference image (a template of good leads). A deviation from the template indicates the presence of a defect. The use of a video camera in an automated inspection system for inspecting the rows of pins on integrated circuit packages of the DIP (Direct Inline Package) type is described in U.S. Pat. No. 4,696,047. It should be noted that the leads on the DIP packages are much thicker with far more spacing between them as compared to Quad packs. There are a number of problems associated with this technique. The size and spacing of leads on VLSI chip requires very high resolution cameras to capture a usable image. This increases the cost and complexity of the system. In addition, the camera has to be synchronized with the movement of each lead under inspection. Image processing and comparison requires large amounts of computing power and time. Thus, this system can be slow and expensive.

Another solution proposed is the use of a plane of light for producing reflected images of the leads as shown in U.S. Pat. No. 5,212,390. This system directs a plane of light onto the leads, and the reflected image is captured by an optical sensor, such as a camera, and then analyzed by a computer. This method allows the calculation of any displacement in the position of a lead within the plane formed by the plurality of leads. Thus, leads which are bent out of the common plane can be detected. However, this system suffers from the aforementioned problems. This system utilizes a very high resolution camera and a computer to process the image. In addition, this system requires interruption of the assembly process to allow for the image to be captured and processed.

Yet another solution proposed is an electro-optical system for detecting selected geometrical properties of the leads on SMT packages are disclosed in U.S. Pat. Nos. 4,875,778 and 4,875,779. The '778 patent discloses a horizontally arranged linear array of photosensitive elements which are moved in a direction perpendicular to a reference surface and operated to provide a series of one dimensional horizontal scans along the leads. The system disclosed in '779 employs a vertically arranged linear array of photosensitive elements which are carried horizontally parallel to a reference surface and operated to provide a series of one dimensional scans vertically along the leads. The chip is placed on a flat test surface and the illumination is provided from within the test surface so as to outline the leads. The linear array of photosensitive elements is moved to scan and detect the light escaping from between the spaces in the leads and any light which escapes from the space between the end of a lead and the flat reference test surface. The analog output signal from the array is converted to a digital signal and is then fed to a microcomputer. The microcomputer analyzes the signal to identify changes in the light intensity values along the linear array. This approach also has some drawbacks. Each chip under inspection has to be first placed on the test surface, and the signal has to be analyzed by the microcomputer.

Another inspection technique is described in U.S. Pat. No. 5,162,866. In this system, the chip under inspection is placed flat onto a IC setting table so that the leads can be irradiated and viewed from the top. A laser beam is used to irradiate both the leads and the surface of the IC setting table. This surface has reference marks present on it. The light source and a photodetector are moved over the IC table so as to scan the leads and the table surface. The reflected light from the leads and the reference marks is used to extract information about any pitch deviations of the leads. Deviation in the planar direction can be detected on the basis of a timing change in the output of the optical sensor. This system requires accurate timing and intensity measurements.

U.S. Pat. Nos. 5,309,223 and 5,331,406 describe a laser based semiconductor lead measurement system. A multi-beam laser system is used to sense the position and condition of each of the many leads used on integrated circuits prior to their placement on a surface mount circuit board. Each lead is passed nominally through the focal point of a laser beam. The position of each lead is determined when it blocks all or a portion of the light of the laser beam. A processor means is used to calculate the actual position of each lead. The position of each lead is then sorted to determine the greatest deviation of any lead from a best fit line or from the seating plane. The processor then generates a reject, pass or repositioning signal. This system is designed to basically assist the pick and place machine in properly aligning the integrated circuits on to the circuit board. Again, as with many of the techniques described above, a processor is needed to calculate the condition of the leads.

It is among the objects of the present invention to provide an improved lead inspection technique that addresses and solves these and other problems of prior art lead inspection techniques.

SUMMARY

Applicant's invention utilizes light diffraction through a periodic pattern (series of leads) to form an approximate uniform image. A deviation in the approximate uniform image of the periodic pattern indicates the presence of damaged leads.

The leads on VLSI chips form a natural periodic pattern. Coherent light passing through the spaces between leads will be diffracted into multiple orders at different angles. For a plane wave, the components of these orders along the direction of the wave will have differing wavelengths depending on the order angle. Because the leads form a natural periodic pattern in one dimension, the diffracted light orders will add coherently at periodic intervals to form images of the original periodic pattern. The effect, known as self imaging, was first observed by H. F. Talbot in 1836 and was explained by Lord Rayleigh in 1881. The latter showed that for a plane wave incident at right angles, the distance between self images of the periodic structure is $2d^2/\lambda$, where d is the grating period and $\lambda$ is the wavelength of the light. If the light is not passing at normal incidence (right angles) through the periodic structure, but rather at an angle $\theta$, the distance is $2(d \cos \theta)^2/\lambda$ ($\theta$ is assumed to be in the plane which contains the normal and the line through the periodic structure). Applicant has observed that at one quarter of the self imaging distance, there is a uniform signal across the field when the periodic pattern is undamaged. Due to interferometric effects of the order of one micron, the wavelength of the light, there is a significant signal when there is even a very small deviation from a precise periodic structure.

A simplified explanation follows. Plane wave coherent light, after passing through a periodic structure, may be represented by a sum of sinusoids having different frequencies (or exponential terms) in a Fourier series:

$$f(x) = \Sigma_n a_n \exp[i 2\pi n x/d] \qquad (1)$$

where d is the period of the periodic structure, x is along the periodic structure, $a_n$ is the amplitude of the nth diffraction order, and i is the square root of $-1$. As the period of the structure is much greater than the wavelength of light, the diffracted energy remains close to the z axis taken to be the direction of propagation of the original light. However, because the components of the different diffraction orders along the z axis have different frequencies, the terms in the sum will interfere with each other as they propagate along the z axis. After diffraction through a distance z, the light field can be written (see equation 2.28 in K. Petorski, "Self imaging phenomena and its application" in Progress in Optics Volume XXVII, Ed E Wolfe, 1989):

$$y(x,z) = \Sigma_n a_n \exp\left[i\pi\lambda \frac{n^2}{d^2} z\right] \exp\left[i 2\pi n \frac{x}{d}\right] \qquad (2)$$

Exponential forms independent of n are neglected because we are interested only in intensity. For self imaging, $z=z_s$ is selected so that the first exponential term in equation (2) is one for every diffraction order n. At this distance (or multiples of this distance) $y(x, z_s) = f(x)$, producing an exact image (equation (1)) of the input periodic structure. The diffraction orders are adding constructively to reconstruct the original periodic structure. The first exponential term in equation (2) becomes one for every diffraction order n when the exponent is $2\pi m$, where m is an integer. Therefore self imaging occurs at periodic intervals of:

$$z_s = 2d^2/\lambda \qquad (3)$$

The periodic structure of VLSI leads may be represented by a square wave. Assuming equal width leads and spaces, this can be written (see W. Siebert, Circuits, Signals and Systems, McGraw-Hill, 1986, equation 12.3–8):

$$f(x) = \frac{1}{2} + \Sigma_{\substack{n=1 \\ n \text{ odd}}} \frac{2(-1)^{(n-1)/2}}{\pi n} \cos 2\pi \frac{n}{d} x \qquad (4)$$

From equation (3), a quarter distance to the self image is defined by the following equation:

$$z_q = z_s/4 = d^2/(2\lambda) \qquad (5)$$

The distance along the light beam from the lead plane to the detector plane is effectively reduced to $(d \cos \theta)^2/(2\lambda)$ if the light is not passing at normal incidence (right angles) through the periodic structure. As used herein the distance $z_q$ is the distance in terms of optical path and not necessarily physical distance. After diffraction, equation (4) is multiplied by the first exponential term of equation (2). Multiplicative phase forms independent of n are neglected because we are interested only in intensity. Using equation (5) to replace z we obtain:

$$y_q(x,z_q) = \frac{1}{2} + \Sigma_{\substack{n=1 \\ n \text{ odd}}} \exp\left[i\frac{\pi}{2} n^2\right] \frac{2(-1)^{(n-1)/2}}{\pi n} \cos 2\pi \frac{n}{d} x \qquad (6)$$

As n is odd and the square of an odd number is also odd, the exponential term in equation (6) is always imaginary with amplitude one. Therefore, all the terms in the summation are imaginary and the summation becomes i times the square wave f(x) of equation (4) but with the DC component removed. The square of a unit amplitude square wave with zero DC component is constant at 0.25. As a result the intensity at the quarter self image distance $y_q y_q^* = |y_q|^2 =$ (real part)$^2$+(imaginary part)$^2 = 0.5^2 + 0.25 = 0.5$ and shows no variation in x and thus no sign of the periodic pattern. The phases from all diffraction orders must exactly match to achieve this uniform result.

Any deviation from the periodic structure of the leads results in a significant local change in uniformity due to a change in diffraction. The wavelength is approximately 0.6 microns so that a change of less than one millionth of a meter can cause an interference fringe to move from destructive to constructive interference, producing a noticeable signal. As the effect is local to the relative position of the damaged leads, only a few leads are needed to establish the periodic structure adequately for this process. Laboratory experiments and computer simulations described below illustrate this effect.

Applicant's invention allows lead inspection to be carried out while the component is in motion. Thus, there is no need to stop or interrupt the assembly process while the actual inspection is being carried out. In fact, inspection can be carried out after the chip is picked up by the placement arm. This is possible because an inspection is completed within 0.5 microseconds with inexpensive components. As mentioned above, parts on the fastest assembly machine move at approximately 2 meters per second. Therefore, during inspection, one part will move only 1 micron, a distance too small to have an adverse effect on applicant's inspection system. In fact, this invention can easily accept much higher assembly speeds by utilizing faster electronics.

It will be understood that the relative "movement" of the leads in the inspection system hereof can be implemented using an array for the source and/or detector. For example, a linear array of photodetectors along the direction of the leads can be placed in the detector plane and the laser source pulsed. In this case, the laser should be wide enough to cover all the leads at once. The array may be housed in a single chip so that it may be envisioned as one detector with elements rather than many detectors in a row. Computer simulation suggests that the number of detectors approximates the number of leads. This is at least an order of magnitude less than would be required in a vision system with similar performance because a vision system has to be able to observe the smallest defect to be detected, needing at least twenty elements per lead period. The outputs of the detectors can be processed by averaging to find the mean. Each detector is squared and the square of the mean subtracted. A level exceeding a threshold, set appropriately above the square mean, indicates a damaged lead. The anticipated level of noise and the acceptable level of lead distortion can be used to determine the amount the threshold is set above the average.

Alternatively, or in addition, instead of squaring values, a differential computation may be used for effectively detecting skewed leads. In this case each detector output is subtracted from that on either side. The resultant values are then thresholded with appropriate thresholds in a similar manner as described above (but with different threshold values).

A further consideration arises if a charge coupled device is used. These are widely available in 1-D and 2-D arrays (used in vision cameras). A 1-D device, as used in conjunction with applicant's invention, would be normally read out sequentially from one end. In this case the detector outputs are converted into a time sequence and the processing can be identical to that used for the case of moving leads relative to the light beam.

Different chips can be taken into account as previously described by having a detector size selected from the smallest lead period and the number of detectors (or elements in the array) determined by the largest period. In the case of large periods, neighboring detectors are summed to emulate larger width detectors.

Applicant's invention also eliminates the need for complicated computer processing by delivering results within the inspection interval of 0.5 microseconds. Since the inspection interval is only 0.5 microseconds, mechanical vibrations will not affect the inspection process since typical mechanical vibrations have time periods much larger than 0.5 microseconds. This invention detects deviation from a periodic structure as a means of inspection. The periodic structure is generated for each set of leads as they pass through the system and the inspection process detects defects if there are any deviations present in this periodic structure. Thus there is no need for a template representing good leads. Accurate alignment or lead positioning is not required. Leads on a tilted VLSI chip still act as a periodic structure. In some situations, a tilt of the light with respect to the periodic structure may be desirable to improve diagnosing certain defects such as lack of coplanarity.

Further features and advantages of the invention will become more readily apparent from the following detailed description when taken in conjunction with the accompanying drawings.

BRIEF DESCRIPTION OF THE DRAWINGS

FIG. 3b is a photograph taken at a quarter self image of the leads of the FIG. 3a.

FIG. 4b is a photograph taken at a quarter self image of the leads of the FIG. 4a.

FIG. 5b is a photograph taken at a quarter self image of the leads of the FIG. 5a.

FIG. 6b shows the computer simulated output of a detector that moves across the diffraction image resulting from the lead configuration of FIG. 6a.

FIG. 7b shows the computer simulated output of a detector that moves across the diffraction image resulting from the lead configuration of FIG. 7a.

FIG. 8b shows the computer simulated output of a detector that moves across the diffraction image resulting from the lead configuration of FIG. 8a.

DETAILED DESCRIPTION

Figure 1:
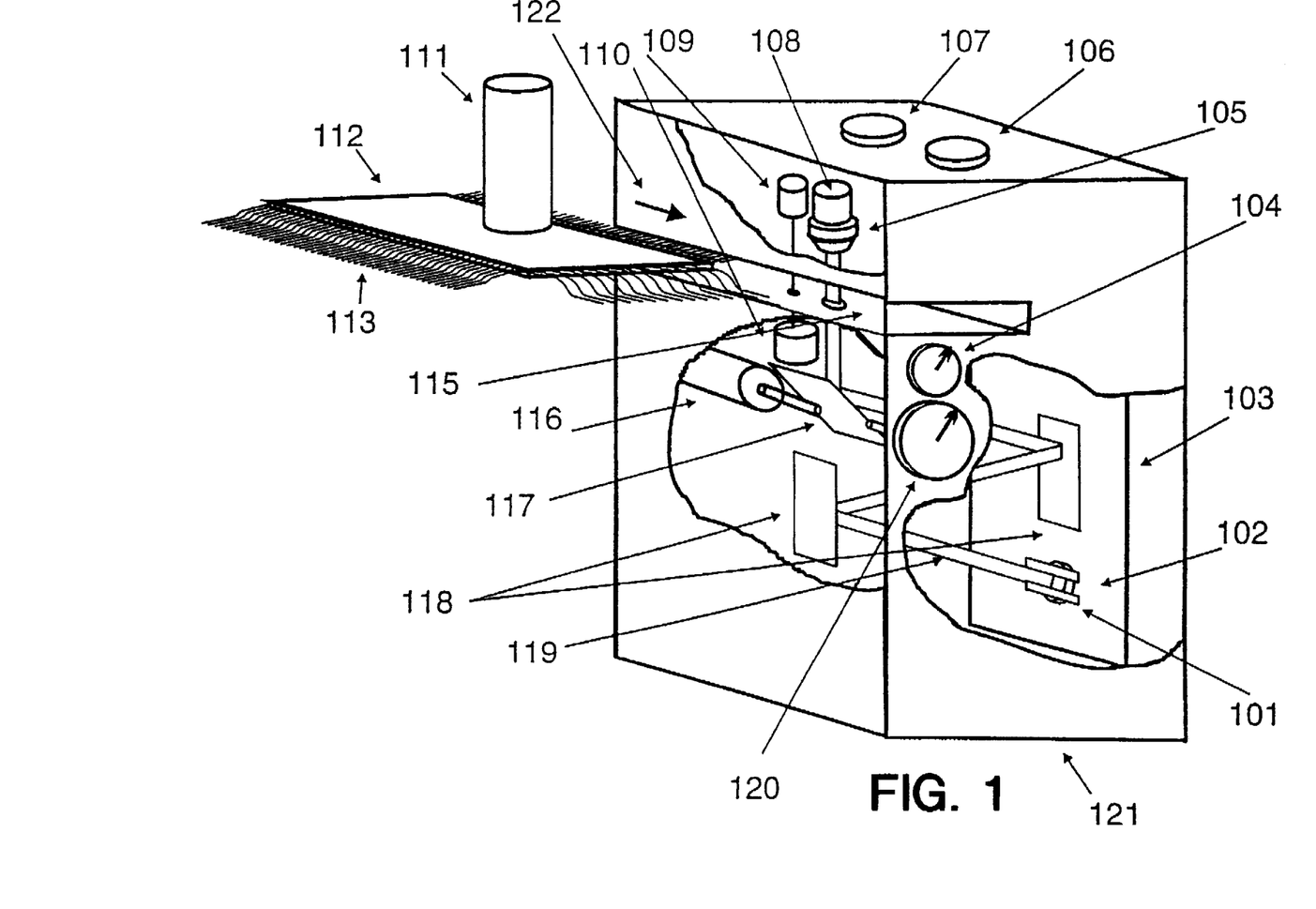
FIG. 1 is a schematic diagram of an apparatus that can be used in practicing an embodiment of the invention.
Figure 2:
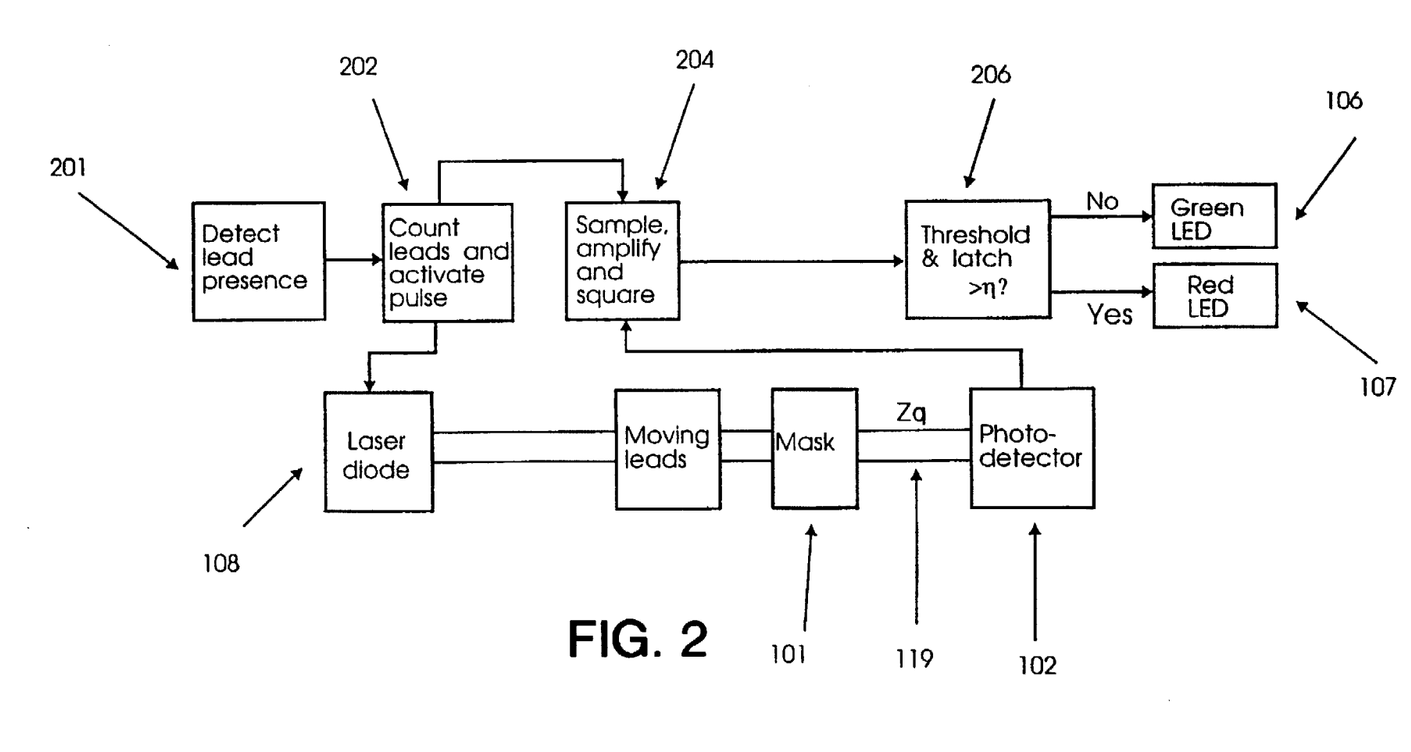
FIG. 2 is a flow diagram of a technique in accordance with an embodiment of the invention.

An embodiment of Applicant's invention is illustrated in conjunction with FIG. 1 for the inspection of leads 113 in VLSI chips 112. The flow diagram of FIG. 2 is also referenced when appropriate. In this particular embodiment, the components include: a laser diode 108 such as those mass produced for CD players, a collimating lens 105 attachment for the laser diode 108, so as to illuminate a sequence of four or so leads 113 with a plane wave, a laser diode driver (not shown) on a circuit board 103 that generates a short electronic pulse 202, a photodetector 102 to collect the signal light 119, electronic circuitry on circuit board 103 to perform: sampling, amplification and, squaring 204, thresholding 205 & 206, and latching 206, an LED control (not shown), a red LED 107 for indicating lead damage and a green LED 106 for indicating absence of lead damage, a light emitter 109 and photodetector 110 pair, a lead counter (not shown) on circuit board 103 for counting (202) leads 113 and activating the laser diode driver, electronic interface for a PC (not shown), control mirror 117, for setting distance between leads 113 (when intercepting light beam 119) and photodetector 102, manual mirror selection control 120 and a control mirror motor 116 for automatic adjustment of mirror 117..

The system unit 121 has a slot 115 like a credit card reader. As the leads 113 pass along the slot 115, in a direction represented by the arrow 122, a light emitter 109 photodetector 110 pair detects (201) leads 113. The output of the photodetector 110 is used to pulse (202) the laser diode 108, starting at a time such that beam 119 passes through the first four leads 113. A 0.5 microsecond pulse is used so that the chip 112, carried by spindle 111, does not have to stop moving and the system is robust against vibration. Collimated light 119, from the laser diode 108, passes through four or so leads 113 to the signal photodetector 102. The detector area should be adjusted between large and small lead periods for good performance. Computer simulations indicate that the detector width w, in the direction along the leads should be in the order of the size of the lead period d (i.e., w=d). A square detector can be used. Altering the detector size can be accomplished by the use of a mask 101 which covers a larger area of the detector from light when inspecting smaller lead periods. In such a case, the mask acts like a square aperture in a similar manner as a camera aperture. Alternatively, an array of detectors may be used. In this case, detectors are selected and summed in groups. For example, four small square detectors can be arranged to form a larger square. One detector is used for small lead periods. For lead periods of twice the size, we sum the four detectors to emulate a detector having twice the side length. The output of the photodetector 102 is electronically sampled, amplified, and squared 204. If this is then above a threshold 206, a latch 206 is activated and the red LED 107 is lit to indicate that a damaged lead 113, has been detected. If this threshold is not exceeded, the green LED 106 is lit indicating undamaged leads 113. For the case where four leads are covered by the laser beam 119 and the leads 113 are adequate to activate the emitter 109 detector 110 pair, every lead 113 can be observed by four different pulses 119. In a preferred embodiment the diode would additionally be pulsed at a high rate (greater than 5 MHz), and a corresponding frequency filter in the detector circuit can be used to make the detector insensitive to room light variations. A rotating mirror 117 may be adjusted manually to set the distance between the leads 113 and photodetector 102 according to equation (5). The adjustment is discretized so that each position allows one or more additional reflections between the two vertical mirrors 118. A motor 116 can allow this adjustment to be set by the computer for the case where the part type is known in the computer, as in an assembly machine. In this case the computer can be used to inform the electronics of the number of leads on this side of the part. A manual adjustment knob 104, can also serve this purpose. The maximum range of lead periods currently planned is 200 microns to 1,300 microns. Therefore the range of distance between leads 113 and photodetector 102 from equation (5) is from 3.2 cm to 1.3 m for a wavelength of 633 nm. The analysis is set forth for the case where the lead width equals the gap width between the leads, but can apply in different arrangements that result in a periodic structure.

Figure 3A:
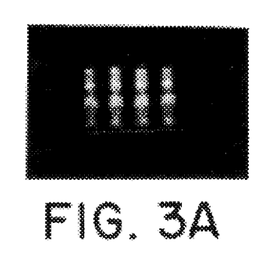
FIG. 3a is a photograph of four undamaged leads.
Figure 3B:
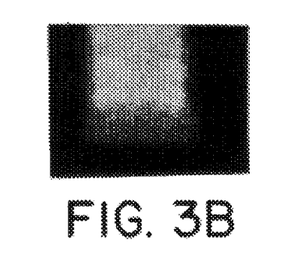
Figure 3C:
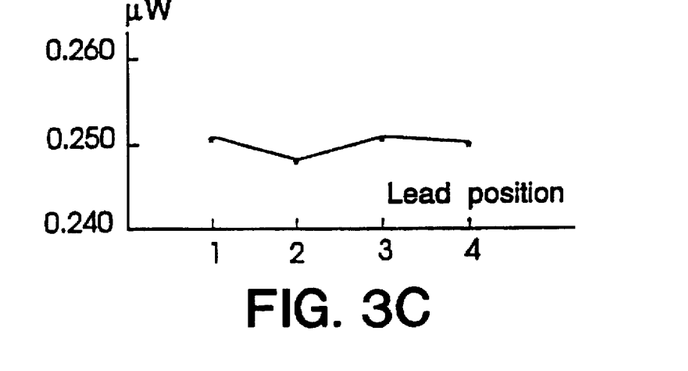
FIG. 3c is a plot of an electronic output of the photodetector as the undamaged leads pass through the system.

FIGS. 3–5 are experimental results obtained in utilizing applicant's invention in inspecting damaged and undamaged leads. FIG. 3a is a photograph of four undamaged leads. FIG. 3b is a photograph showing uniform intensity across the diffraction image at a distance of a quarter of the self image for the leads shown in FIG. 3a. The white box shows the detector size used to scan the diffraction image as the leads move through the light beam. The arrow shows the relative direction of the detector with respect to the diffraction image as the leads move through the light beam. The output of a detector represented by the white box in FIG. 3b as the leads move through the beam is seen in FIG. 3c. The electronic output of the system is shown in the y axis, while the x axis represents the lead positions moving left to right in the path of the light. The detector output is proportional to the average of the intensities falling in the area of the white box times the area of the box. The output is seen to be approximately constant as the leads move over the detector. Small deviations from constant may be due to small deformities in the leads because the system is more sensitive than the human eye.

Figure 4A:
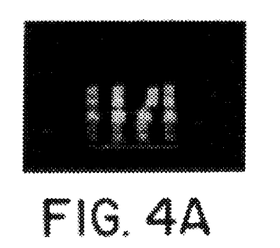
FIG. 4a is a photograph of four leads with one damaged lead bent sideways.
Figure 4B:
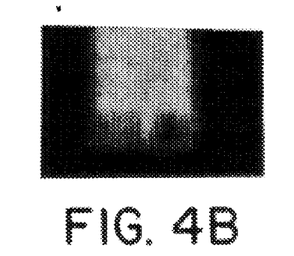
Figure 4C:
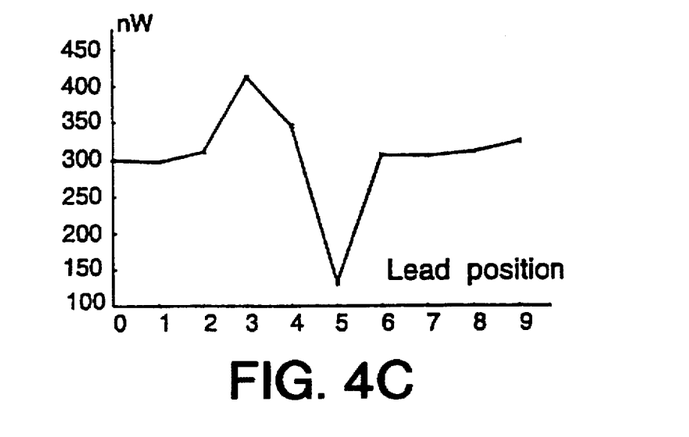
FIG. 4c is a plot of an electronic output of the photodetector as the damaged lead of FIG. 4a passes through the system.

A photograph of four leads with one lead deformed by skew (or sideways bending) is seen in FIG. 4a. FIG. 4b is a photograph of the diffraction image at a distance of a quarter of that for self image for the leads of FIG. 4a. The image is seen to vary in intensity from left to right with variation going from light at the center to dark at the right of center. The measured output of a detector represented by the white box in FIG. 4b is seen in FIG. 4c as the leads move across the detector. The more than 50% variation of amplitude from average caused by the variation from light to dark in FIG. 4b, indicates the presence of a skewed lead.

Figure 5A:
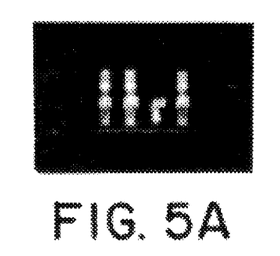
FIG. 5a is a photograph of four leads with one damaged lead bent downward.
Figure 5B:
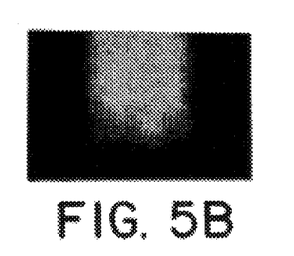
Figure 5C:
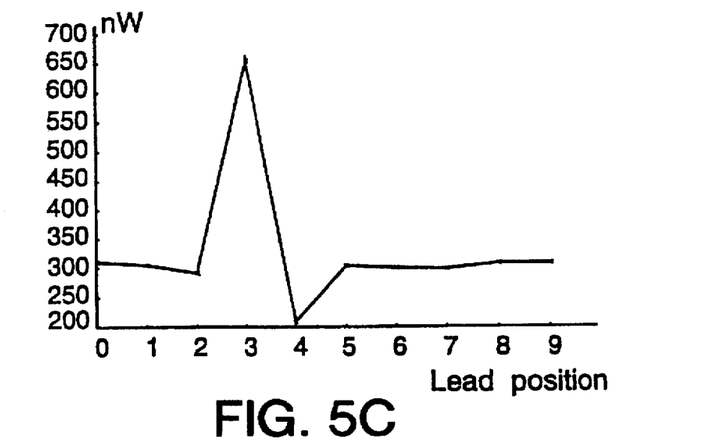
FIG. 5c is a plot of an electronic output of the photodetector as the damaged lead of FIG. 5a passes through the system.

FIG. 5a is a photograph of four leads in which one is bent down, used for laboratory experiments to verify detection of lack of coplanarity. FIG. 5b is a photograph of the diffraction image at a distance of a quarter of that for self image for the leads of FIG. 5a. The image is seen to have a bright part in the center when moving from left to right. The measured output of a detector represented by the white box in FIG. 5b as the leads move across the detector is shown in FIG. 5c. The greater than 100% peak relative to the average provides significant information for detecting short or bent down leads.

Figure 6A:
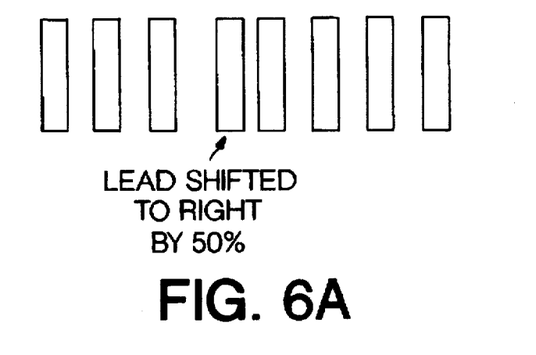
FIG. 6a shows an image of four leads used for computer simulation in which one lead is shifted by half its width.

FIGS. 6–8 represent computer simulations representing three types of lead deformities. FIG. 6a shows an image of four leads used for computer simulation in which one lead is shifted by half its width. This also represents the case of the top half of a lead shifted as the detector can be set to view only the top halves of the leads.

Figure 6B:
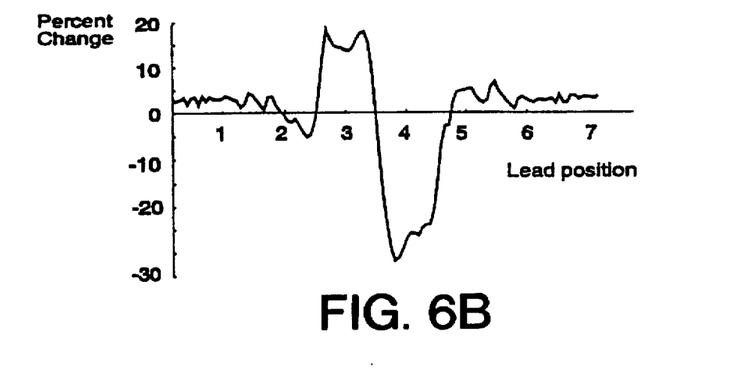

FIG. 6b shows the computer simulated output of a detector that moves across the diffraction image resulting from the lead configuration of FIG. 6a. The diffraction image is at a distance of a quarter of that for self image of the leads. A differential (maximum minus minimum) variation of almost 50% indicates that a signal can be developed with a percentage change comparable to the percentage shift in lead deformation. The amplitude and shape of the response are consistent with the experimental results of FIG. 4c.

Figure 7A:
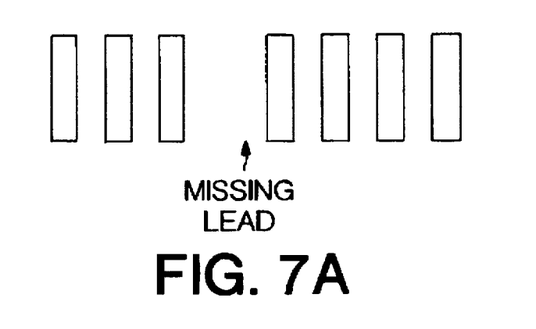
FIG. 7a shows an image of four leads used for computer simulation in which one lead is missing.

FIG. 7a shows an image of four leads used for computer simulation in which one lead is missing. This also represents the case of the top half of a lead missing as the detector can be set to view only the top halves of the leads.

Figure 7B:
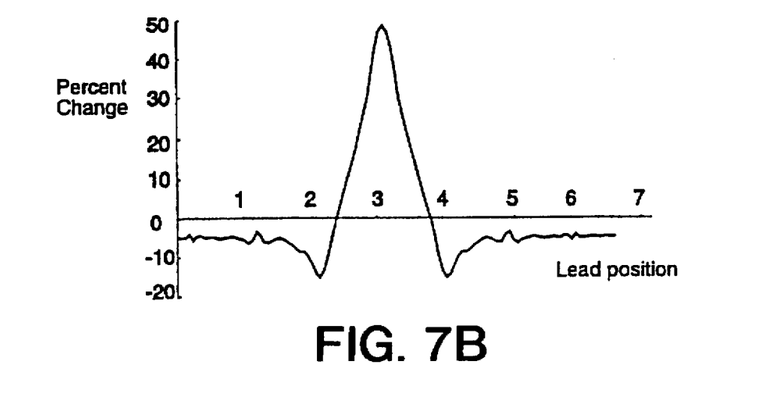

FIG. 7b shows the computer simulated output of a detector that moves across the diffraction image resulting from the lead configuration of FIG. 7a. The diffraction image is at a distance of a quarter of that for self image of the leads. Variations of approximately 50% and the shape of the response are consistent with the experimental results of FIG. 5c.

Figure 8A:
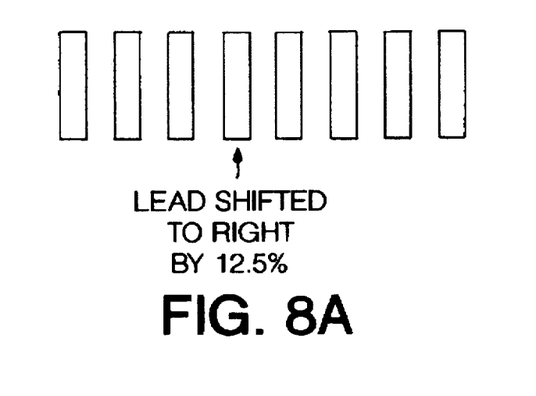
FIG. 8a shows an image of four leads used for computer simulation in which one lead is shifted by 12.5% of its width.

FIG. 8a shows an image of four leads used for computer simulation in which one lead is shifted by 12.5% of its width. For a 100 micron wide lead this represents only 12.5 microns making the deformity invisible to the naked eye but close to the limits required for a lead inspection system.

Figure 8B:
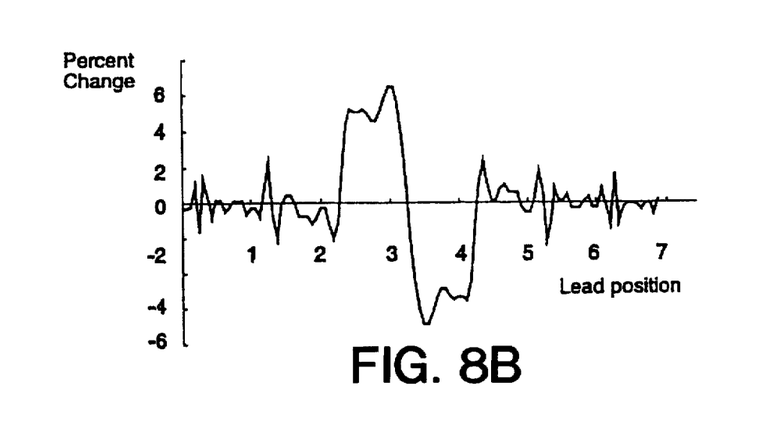

FIG. 8b shows the computer simulated output of a detector that moves across the diffraction image resulting from the lead configuration of FIG. 8a. The diffraction image is at a distance of a quarter of that for self image of the leads. A differential (maximum minus minimum) variation of almost 12% indicates that a signal can be developed with a percentage change comparable to the percentage shift in lead deformation. This confirms the approximately linear relations observed in describing FIG. 6b.

Figure 9:
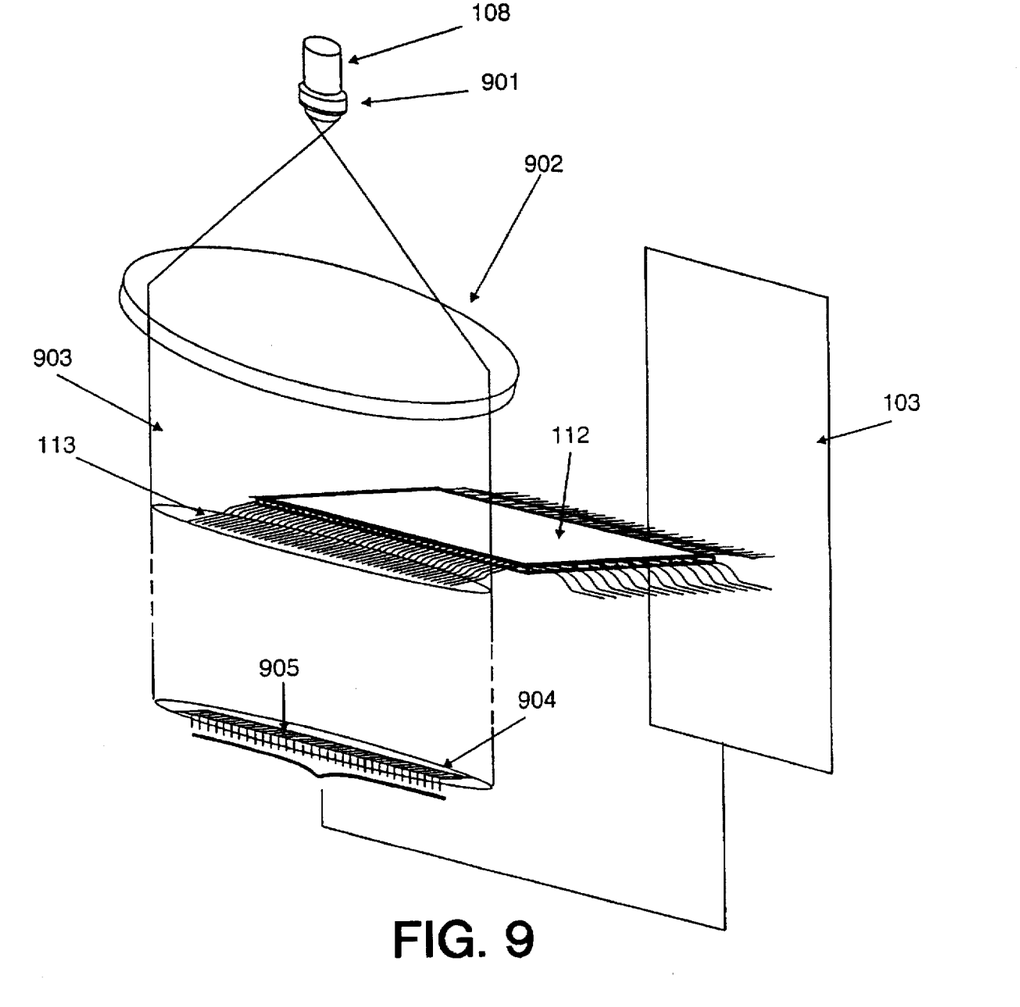
FIG. 9 is a schematic of an apparatus for simultaneous inspection of leads in practicing an embodiment of the invention.

FIG. 9 shows an apparatus for simultaneous inspection of all leads on one edge of a chip. Light from laser diode 108 passes through a short focus lens (not shown) in a housing 901 and a collimating lens 902. A laser diode can generate an oval shaped beam 903. A fan beam (not shown), with narrower waist, can be used to increase the percentage of light falling on the detector, but requires special optics. The beam 903 illuminates the top part of all leads 113 on one edge of the chip 112. A detector array 904 is placed at a quarter of the self image distance from the leads 113. The signal from each array element 905 of the detector array 904 may be passed to electronic circuit board 103, squared and the average computed. This average is then subtracted from each element squared signal. A threshold is set at some percentage above the average. Leads are considered damaged if the threshold is exceeded and undamaged if the threshold is not exceeded.

The invention has been described with reference to particular preferred embodiments, but variation within the spirit and the scope of the invention will occur to those skilled in the art.

We claim:

1. A method for detecting damage of leads arranged in a generally parallel periodic pattern, comprising the steps of:
   (a) directing a coherent light beam at a plurality of adjacent leads;
   (b) detecting an image at a distance from the leads at which said light beam would form a diffraction image having substantially uniform intensity when said leads form a substantially uniform pattern;
   (c) moving said pattern of leads and said light beam with respect to each other; and
   (d) detecting damage of leads from variation in intensity of the detected image.

2. The method as defined by claim 1 wherein said diffraction image is formed at the quarter self image distance of the leads.

3. The method as defined by claim 1 wherein said distance is $z_q$, and $z_q$ is determined by the equation:

$$z_q = d^2/(2\lambda),$$

where d is the lead period, and $\lambda$ is the wavelength of the coherent light beam.

4. The method as defined by claim 1 wherein said distance is $z_q$, and $z_q$ is determined by the equation:

$$z_q = (d \cos \theta)^2/(2\lambda)$$

where d is the lead period, $\lambda$ is the wavelength of the coherent light beam, and $\theta$ is the angle with respect to the normal to the plane of the leads.

5. The method as defined by claim 1 wherein said coherent light beam is a laser.

6. Apparatus for detecting damage of leads arranged in a generally parallel periodic pattern, comprising:
   means for directing a coherent light beam at a plurality of adjacent leads;
   means for detecting an image at a distance from the leads at which said light beam would form a diffraction image having substantially uniform intensity when said leads form a substantially uniform pattern;
   means for moving said pattern of leads and said light beam with respect to each other; and
   means for determining the variation in intensity of the detected image.

7. The apparatus as defined in claim 6, wherein said diffraction image is formed at the quarter self image distance of the leads.

8. The apparatus as defined in claim 6, wherein said means for detecting the image comprises a photodetector.

9. The apparatus as defined in claim 8, wherein the distance of the photodetector from the leads, $z_q$, is determined by the equation:

$$z_q = d^2/(2\lambda),$$

where d is the lead period, and $\lambda$ is the wavelength of the coherent light beam.

10. The apparatus as defined in claim 8, wherein the distance of the photodetector from the leads, $z_q$, is determined by the equation:

$$z_q = (d \cos \theta)^2/(2\lambda),$$

where d is the lead period, $\lambda$ is the wavelength of the coherent light beam, and $\theta$ is the angle with respect to the normal to the plane of the leads.

11. The apparatus as defined in claim 8, wherein said means for detecting the image further comprises a threshold detector coupled with the output of said photodetector.

12. The apparatus as defined in claim 11, wherein said means for detecting the image further comprises a mirror located in path of said light beam between said leads and said detector.

13. The apparatus as defined in claim 12, wherein said mirror is adjustable.

14. Apparatus for detecting damage of leads arranged in a generally parallel periodic pattern, comprising:
   means for directing a coherent light beam at plurality of adjacent leads;
   means for detecting an image at a distance from the leads at which said light beam would form a diffraction image having substantially uniform intensity when said leads form a substantially uniform pattern, said means for detecting an image comprising a photodetector array; and
   means for determining the variation in intensity of the detected image.

15. The apparatus as defined in claim 14, wherein said diffraction image is formed at the quarter self image distance of the leads.

16. The apparatus as defined in claim 14, wherein the distance of the photodetector array from the leads, $z_q$, is determined by the equation:

$$z_q = d^2/(2\lambda),$$

where d is the lead period, and $\lambda$ is the wavelength of the coherent light beam.

17. The apparatus as defined in claim 14, wherein the distance of the photodetector array from the leads, $z_q$, is determined by the equation:

$$z_q = (d \cos \theta)^2/(2\lambda),$$

where d is the lead period, $\lambda$ is the wavelength of the coherent light beam, and $\theta$ is the angle with respect to the normal to the plane of the leads.

18. The apparatus as defined in claim 14, wherein said means for detecting the image further comprises a threshold detector coupled with the output of said photodetector array.

19. The apparatus as defined in claim 18, wherein said means for detecting the image further comprises a mirror located in path of said light beam between said leads and said detector.

20. The apparatus as defined in claim 19, wherein said mirror is adjustable.

* * * * *